United States Patent [19]
Serbiak et al.

[11] Patent Number: 5,807,362
[45] Date of Patent: *Sep. 15, 1998

[54] ABSORBENT ARTICLE

[75] Inventors: Paul John Serbiak; Annamaria Cesco-Cancian, both of Appleton; Julie Kathleen Fredrick, Larsen; Robert John Peerenboom, Little Chute, all of Wis.

[73] Assignee: Kimberly-Clark Worldwide, Inc., Neenah, Wis.

[ * ] Notice: The term of this patent shall not extend beyond the expiration date of Pat. No. 5,219,341.

[21] Appl. No.: 218,954

[22] Filed: Mar. 28, 1994

Related U.S. Application Data

[63] Continuation of Ser. No. 48,640, Apr. 16, 1993, abandoned, which is a continuation of Ser. No. 811,388, Dec. 20, 1991, Pat. No. 5,219,341.

[51] Int. Cl.[6] ............................. A61F 13/42; A61F 13/46
[52] U.S. Cl. .............................. 604/361; 604/378
[58] Field of Search .................... 604/361, 378, 604/381, 379, 383

[56] References Cited

U.S. PATENT DOCUMENTS

| | | |
|---|---|---|
| 1,863,333 | 6/1932 | Heitmeyer . |
| 1,910,872 | 5/1933 | Williams . |
| 2,047,054 | 7/1936 | Beyer, Jr. . |
| 2,154,332 | 4/1939 | Hirsch . |
| 2,787,271 | 4/1957 | Clark . |
| 3,397,697 | 8/1968 | Rickard . |
| 3,857,394 | 12/1974 | Alemany . |
| 4,069,822 | 1/1978 | Buell . |
| 4,079,739 | 3/1978 | Whitehead . |
| 4,282,874 | 8/1981 | Mesek . |
| 4,285,343 | 8/1981 | McNair . |
| 4,327,731 | 5/1982 | Powell . |
| 4,372,312 | 2/1983 | Fendler et al. . |
| 4,433,972 | 2/1984 | Malfitano ................. 604/385 |
| 4,507,121 | 3/1985 | Leung ...................... 604/361 |
| 4,540,414 | 9/1985 | Wishman ................. 604/378 |
| 4,589,876 | 5/1986 | Van Tilburg ........... 604/385 R |
| 4,608,047 | 8/1986 | Mattingly ................ 604/387 |
| 4,627,848 | 12/1986 | Lassen et al. ........... 604/370 |
| 4,687,478 | 8/1987 | Van Tilburg ............. 604/387 |
| 4,738,674 | 4/1988 | Todd et al. .............. 604/361 |
| 4,773,905 | 9/1988 | Molee et al. ............ 604/378 |
| 4,846,829 | 7/1989 | Lloyd ..................... 604/389 |
| 4,880,419 | 11/1989 | Ness ...................... 604/368 |
| 4,950,264 | 8/1990 | Osborn, III ........... 604/385.1 |
| 5,009,650 | 4/1991 | Bernardin ............... 604/378 |
| 5,009,653 | 4/1991 | Osborn, III ........... 604/385.1 |
| 5,037,409 | 8/1991 | Chen et al. ............. 604/358 |
| 5,219,341 | 6/1993 | Serbiak et al. .......... 604/361 |

FOREIGN PATENT DOCUMENTS

| | | |
|---|---|---|
| 0134086A1 | 3/1985 | European Pat. Off. . |
| 0203715A3 | 12/1986 | European Pat. Off. . |
| 0316771A3 | 5/1989 | European Pat. Off. . |
| 2047439 | 9/1970 | Germany . |
| 2144995 | 3/1985 | United Kingdom . |
| 2161384 | 1/1986 | United Kingdom . |
| WO91/14415 | 10/1991 | WIPO . |

*Primary Examiner*—David H. Willse
*Attorney, Agent, or Firm*—Thomas J. Connelly

[57] ABSTRACT

An absorbent article, such as a sanitary napkin, is disclosed which is designed to absorb menstrual fluid. The absorbent article includes a liquid-impermeable baffle, a first absorbent layer and a second absorbent layer. The second absorbent layer is positioned between the baffle and the first absorbent layer and has a higher transverse wicking rate than the first absorbent layer. The absorbent article can be visually inspected to determine if it is linear its maximum fluid capacity before leakage occurs.

12 Claims, 5 Drawing Sheets

ABSORBENT ARTICLE

This is a continuation application of application Ser. No. 08/048,640, filed on Apr. 16, 1993, now abandoned, which is a continuation application of application Ser. No. 07/811,388, filed Dec. 20, 1991, which has issued to U.S. Pat. No. 5,219,341.

FIELD OF THE INVENTION

This invention relates to an absorbent article for absorption of menstrual fluid. It is particularly directed to sanitary napkins.

BACKGROUND OF THE INVENTION

Absorbent articles, classified as sanitary napkins, catamenial pads or feminine pads, are designed to be worn by a female to absorb menstrual fluids and other excrements discharged by the body during a menstrual period. Sanitary napkins are external devices which are generally held in position by an adhesive or by a mechanical attachment to an undergarment. Such products differ from tampons which are classified as internal devices and which are designed to be physically inserted into the vagina. Functionally, sanitary napkins are different from other external devices, such as pantiliners or panty shields, in that they are generally constructed to absorb a greater quantity of body fluid and are designed to be worn for a longer period of time; for example, overnight if needed.

In order to adequately perform their function, modern sanitary napkins are constructed of highly absorbent materials. However, if any absorbent material is utilized to, or near, the point where it becomes fully saturated, there is a possibility that leakage of body fluid could occur which might stain the user's clothing.

It is, therefore, desirable to construct an absorbent article which could be visually examined to determine if it is near its fluid-saturation point. Quite often, the absorption of body fluids is into a target zone on the top of the product; and it is not clear, from looking at the top of the product, if the product is close to being saturated. It is also difficult to tell when the target area is so close to being fully saturated that leakage may soon occur.

Therefore, there is a need to provide an absorbent article which can provide the user with a quick visual inspection to determine if it is near its absorption limits. If the product is close to its limit, the user could then replace it before leakage occurs.

There are several United States patents which teach the advantages of using an absorbent material which has good fluid-wicking properties for at least a portion of the absorbent layer. U.S. Pat. No. 4,732,312 issued to Fender et al. teaches an absorbent pad containing a nonwoven hydrophilic thermoplastic filamentary microfiberous web as part of the absorbent material. The microfiberous web exhibits good wicking and fluid-retention properties. The microfiberous web is not used to provide an indication that the pad is close to absorbent capacity.

A second patent, U.S. Pat. No. 3,525,338 issued to Bernardin, discloses utilizing a layer of glass microfibers as part of the absorbent material. The glass microfiberous layer has good absorbent capacity and wicking capabilities. When a layer of glass microfibers is deposited horizontally between two layers of conventional absorbent material, the absorbent capacity of the sanitary napkin is increased as well as its efficiency. The latter is due to the lateral wicking properties of the layer of glass microfibers. The use of absorbent materials, having varying transverse wicking rates which can serve as a visual indicator, is not taught in this patent. Furthermore, neither Fender nor Bernardin teach using layers with various wicking rates as a method of providing an indication of the saturation level of an absorbent article.

There is also a need to design an absorbent article, where the crotch portion of the user's undergarment, to which the absorbent article is attached, will not fold onto the body-facing side of the product. This will assist in preventing the undergarment from becoming stained by body fluid. One method of overcoming this problem is to design absorbent articles with flaps or wings which extend outward from the central absorbent. However, the addition of flaps or wings makes the product more expensive. Typically, sanitary napkins having flaps or wings use a central adhesive strip which attaches the product to the crotch portion of a user's undergarment. The side flaps or wings are then folded around the outer surface of the undergarment to protect the undergarment from becoming stained. Some U.S. patents which teach the use of flaps or wings include the following.

U.S. Pat. No. 2,787,271 issued to Clark describes a sanitary napkin comprising a rectangular central pad having a pair of lateral flaps integrally formed with the pad. The flaps are adapted to fold downward and bear against the inner surface of the wearer's thighs. The flaps or wings are designed to stop any overflow of body fluid from staining the user's clothing. The central pad has an absorbent core body which extends without interruption into the lateral flaps.

U.S. Pat. No. 3,397,697 issued to Rickard describes a disposable sanitary shield for undergarments. This shield comprises an elongated sheet of flexible material divided into at least two panels which are joined by an intermediate neck-like portion. Portions of the panels, located adjacent to the neck-like portion, include wing-like flaps which are adapted to be folded over each other. This enables the flaps to encircle the crotch portion of the undergarment and prevent staining.

U.S. Pat. No. 4,285,343 issued to McNair describes a sanitary napkin having a central absorbent pad with laterally extending side panels. The side panels can be formed either integrally with the central absorbent or be formed separately and then secured to the longitudinal edges of the central absorbent.

U.S. Pat. No. 4,687,478 issued to Van Tilburg describes a sanitary napkin having two flaps that extend outward from an absorbent means. The absorbent means is secured in the crotch of a panty, and the flaps are secured about the elastic edges of a panty by an adhesive.

Despite the teachings of the prior art, there is still a need for an absorbent article which can be visually inspected to determine if it is at, or near, its fluid-saturation limit.

SUMMARY OF THE INVENTION

Briefly, this invention relates to absorbent articles, such as sanitary napkins, which are designed to absorb menstrual fluid and other excrements discharged by the body during a menstrual period. The absorbent article provides a user with the ability to quickly determine if it is approaching its saturation limit. The absorbent article includes a liquid-impermeable baffle and first and second absorbent layers. The second absorbent layer is positioned between the baffle and the first absorbent layer and has a higher transverse wicking rate than the first absorbent layer. Consequently, body fluid that works through the thickness of the first absorbent layer spreads in a transverse direction on the second absorbent layer at a faster rate than it does on the first absorbent layer. This feature allows the fluid to reach the outer or lateral edges of the second absorbent layer faster than fluid that remains in the first absorbent layer. The presence of extensive staining, near the side edges of the second absorbent layer, serves as a signal that the product is near its maximum fluid capacity. The second absorbent layer is wider along its central transverse axis than is the first absorbent layer. This assures that the lateral edges of the second absorbent layer are visible to the user when she looks down onto the top of the absorbent article.

The absorbent article can optionally include a third absorbent layer which is positioned between the first and second absorbent layers. The second absorbent layer will be wider, along its central transverse axis, than either the first or the third absorbent layers. When a third absorbent layer is utilized, it will not have as high a transverse wicking rate as the second absorbent layer. This will hold true even when the third absorbent layer functions as the primary absorption layer of the absorbent article.

The general object of this invention is to provide an absorbent article having two absorbent layers, wherein the lower layer has a greater transverse wicking rate than the first layer. A more specific object of this invention is to provide a sanitary napkin which enables the user to visually inspect the product to see if it is approaching its maximum fluid capacity.

Another object of this invention is to provide an absorbent article which is easy to manufacture and is relatively low in cost.

Still another object of this invention is to provide an absorbent article, which utilizes at least two separate and distinct absorbent layers, wherein the upper absorbent layer is narrower in size than a lower layer.

Still further, an object of this invention is to provide an absorbent article which has improved fluid absorbency features.

Other objects and advantages of the present invention will become more apparent to those skilled in the art in view of the following description and the accompanying drawings.

DETAILED DESCRIPTION OF THE INVENTION

Figure 1:
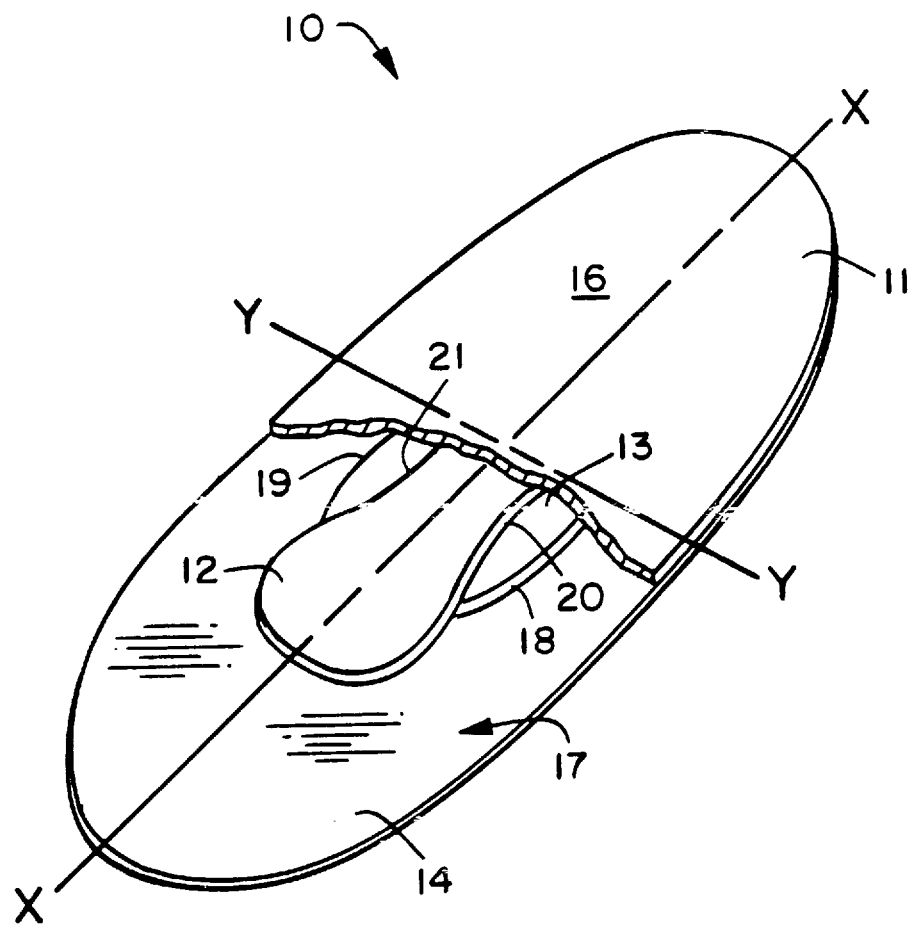
FIG. 1 is a perspective top view of an absorbent article having a portion cut away to show the inner construction thereof.

Referring to FIG. 1, an absorbent article 10 in the form of a sanitary napkin is shown which can be worn by a female to absorb body fluids such as menses, blood, urine, and other excrements discharged during a menstrual period. The absorbent article 10 is about 150 millimeters (mm) to 300 mm long, about 50 mm to 125 mm wide and has a generally oval shape. Other shapes, including hourglass, dogbone and racetrack, are contemplated. The absorbent article 10 should have a caliper or thickness of less than about 15 mm, preferably less than about 10 mm, and most preferably, less than about 5 mm.

The absorbent article 10 includes a bodyside cover 11, which is liquid permeable, a first absorbent layer 12, a second absorbent layer 13 and a liquid-impermeable baffle 14. The first absorbent layer 12 can be hourglass in shape and should not be as long or as wide as the cover 11. The bodyside cover 11 has an upper surface 16 which contacts the body of the user. The first absorbent layer 12 can be secured to, or retained on, the second absorbent layer 13. The second absorbent layer 13 is wider, along its central portion, than the first absorbent layer 12. The second absorbent layer 13 can, in turn, be secured to, or retained on, a top surface 17 of the baffle 14. The baffle 14 should generally have the same dimensions as the bodyside cover 11. The bottom side of the baffle 14 will contact the inner surface of the undergarment worn by the user of the absorbent article 10.

The liquid-permeable cover 11 is designed to contact the body of the wearer and can be constructed of a woven or nonwoven, natural or synthetic, material which is easily penetrated by body fluid. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs and net material, also work well. Particularly preferred are composite materials of a polymer and a nonwoven fabric material. The composite sheets are generally formed by extrusion of the polymer onto a web of spunbond material to form an integral sheet. This material is preferred, because the outer fabric surface is not irritating to the skin of the wearer and has a cushioned feel.

The walls of the absorbent article 10 generally extend up, into the crease between the legs and the pudendum of the wearer, and have a cushioned feel. Therefore, the outer wall portions may come in contact with the legs of the wearer and should provide a comfortable nonirritating feel.

Another preferred material for the cover 11 is a spunbond web of polypropylene. The web can contain about 1 to 6% titanium dioxide pigment to give it a clean, white appearance. A uniform spunbond material is desirable, because it has sufficient strength, after being perforated in the longitudinal direction, to resist being torn or pulled apart during use. The most preferred polypropylene webs have a weight of between about 18 and 40 grams per square meter. An optimum weight is between about 30 and about 40 grams per square meter.

Liquid-permeable covers utilized on absorbent articles, especially sanitary napkins, can be comprised of a white material. White material has good fluid-masking properties and can hide the stain of liquid that has passed through it. However, the advantages of the present invention are best realized if the liquid-permeable cover 11 is sufficiently transparent to enable a user to examine the absorbent article 10 from its top side. This examination will determine if any fluid has spread in a transverse direction, that is, in a direction perpendicular to the longitudinal central axis X—X of the product. The transverse central axis Y—Y of the absorbent article 10 is perpendicular to the longitudinal edges 18 and 19 of the second absorbent layer 13.

The liquid-permeable cover 11 can also contain a plurality of apertures (not shown) formed therein. Such apertures can be arranged along the longitudinal center axis X—X, if desired, and are intended to increase the rate at which body fluids can penetrate down into the first absorbent layer 12.

With apertures present, body fluid, which is deposited at or near the apertures, rapidly migrates into the first absorbent layer 12. This helps maintain a perceivably drier surface than when the apertures are not employed. Therefore, while the apertures are not essential, some functional advantages are obtained.

The liquid-permeable cover 11 can also be treated with a surfactant to make it more hydrophilic and, thereby, aid in the absorption of the liquid. The surfactant can include topical additions or internally applied materials like polysiloxanes.

The baffle 14 permits the passage of air or vapor out of the absorbent article 10 while blocking the passage of body fluids and liquids from the absorbent layer 12 and 13. The baffle 14 can be made from any desired material that has these properties. A good material is a micro-embossed, polymeric film, such as polyethylene or polypropylene. Bicomponent films can also be used. A preferred material is polyethylene film. Most preferably, the baffle 14 will be comprised of a polyethylene film having a thickness in the range of from about 0.5 to about 2.0 mm.

As indicated, the liquid-impermeable baffle 14 is coextensive with the liquid-permeable cover 11 and is adhered to the cover 11 in those areas where the cover 11 and the baffle 14 are in face to face contact. The method of adhering the cover 11 to the baffle 14 may be any suitable method that does not leave a hard, uncomfortable residue that would be annoying to the wearer. Typical of sealing methods are heat sealing and adhesive sealing. Another method is ultrasonically bonding on a line inward from the edge of the absorbent article 10. When this is done, a loose flap or fringe of material usually extends about a quarter inch outward from the bond line about the periphery of the product. This results in a neat bond line with less tendency for the material to be perforated than by heat sealing.

A particular advantage of the absorbent article 10 is that it provides an indicator when it is near to its maximum fluid-saturation point. The indicator begins to function when fluid begins to migrate down into the second absorbent layer 13. As indicated, the second absorbent layer 13 is comprised of a material that has a higher transverse wicking rate than that of the first absorbent layer 12. Body fluid, which reaches the second absorbent layer 13, will migrate in a transverse direction to the outer edges 18 and 19 faster than fluid in the first absorbent layer 12 can reach the longitudinal edges 20 and 21. Therefore, a user can visibly inspect the absorbent article 10 from its top surface to determine if it needs to be replaced. If fluid is detected near the lateral edges 18 and 19 of the second absorbent layer 13, the user will have a clear indication that the absorbent article 10 needs replacing. To facilitate such an inspection, the second absorbent layer 13 should be wider, along its central transverse axis, than the first absorbent layer 12. It should be noted that the central transverse axis of each of the layers, 12 and 13 respectively, will generally line up with the central transverse axis of the absorbent article 10. Preferably, the second absorbent layer 13 should be as visually distinctive as possible from the other layers of the absorbent article 10. One way of achieving this would be to make the second absorbent layer 13 a different color from the other layers. However, care should be taken to utilize a color for the second absorbent layer 13 that would highlight, rather than mask, the presence of fluid thereon.

The cover 11 and the baffle 14 will, in combination, enclose the first absorbent layer 12 and the second absorbent layer 13. The second absorbent layer 13 will be located between the first absorbent layer 12 and the baffle 14. Both layers, 12 and 13 respectively, are comprised of absorbent material. Typically, the first absorbent layer 12 will be comprised of a material that is more absorbent than the material comprising the second absorbent layer 13. As indicated above, the second absorbent layer 13 is comprised of a material that has a higher transverse wicking rate than the material which comprises the first absorbent layer 12. The first absorbent layer 12 will, as the primary absorbent layer, typically be thicker than the second absorbent layer 13. It should be emphasized that the values relating to absorbency and the transverse wicking rate are relative for any particular style of absorbent article. It is, therefore, quite possible that one particular style of absorbent article may utilize the same material in its second absorbent layer as that utilized as the first absorbent layer in another absorbent article.

The absorbent materials used in the absorbent article 10 are designed to absorb body exudates, including menstrual fluids, catamenial fluids, blood and urine. Suitable materials include wood pulp fluff, rayon, cotton and meltblown polymer, such as polyester, polypropylene or coform. Coform is a meltblown air-formed combination of meltblown polymers, such as polypropylene, and absorbent staple fibers, such as cellulose. A preferred material is wood fluff, for it is low in cost, relatively easy to form and has good absorbency.

The absorbent material may be a composite comprised of a hydrophilic material that can be formed from various natural or synthetic fibers, wood pulp fibers, regenerated cellulose or cotton fibers, or a blend of pulp and other fibers. A preferred material is an airlaid tissue. The absorbent layers may also be comprised of other well-known materials used in absorbent articles, including multiple layers of cellulose wadding, rayon fibers, cellulose sponge, hydrophilic synthetic sponge, such as polyurethane, and the like.

The absorbent layers 12 and 13 may contain superabsorbent particles which are extremely effective in retaining body fluids. Superabsorbents have the ability to absorb a large amount of fluid in relation to their own weight. Typical superabsorbents used in absorbent articles, such as sanitary napkins, can absorb anywhere from 5 to 60 times their weight in body fluids. However, the absorption mechanism of the superabsorbents is usually slower than the rate of fluid absorption by cellulose fluff material. The placement of the superabsorbent particles in the central portion of the absorbent article 10 provides additional time for the superabsorbent particles to absorb the body fluid temporarily retained by a transfer member.

It has been found that superabsorbents having a high mechanical stability in the swollen state, an ability to rapidly absorb fluid, and those having a strong liquid-binding capacity perform well in catamenial devices. Hydroxyfunctional polymers have been found to be good superabsorbents for this application. The superabsorbent can be a hydrogel-forming polymer composition which is water-insoluble, slightly cross-linked, and partially neutralized. It can be prepared from unsaturated polymerizable, acid group-containing monomers and cross-linked agents. A hydrogel-forming polymer, which is a partially neutralized crosslinked copolymer of polyacrylic acid and polyvinyl alcohol, is preferred. After a polymer is formed, it is mixed with about a 1% anhydrous citric acid powder. The citric acid has been found to increase the ability of the superabsorbent to absorb menses and blood. This is particularly good for use in a sanitary napkin or feminine pad. The finely ground, anhydrous citric acid powder, which is void of water, along with trace amounts of fumed silica, is mixed with the polymer which has been screened to an appropriate particle size. This mixture can then be formed into a composite or a laminate structure. Such superabsorbents can be obtained from Dow Chemical, Hoechst-Celanese, and Stockhausen, Inc., among others, and are a partially neutralized salt of cross-linked copolymer of polyacrylic acid and polyvinyl alcohol having an absorbency under load value above 25.

One combination of the absorbent layers 12 and 13 is for the first absorbent layer 12 to be made up of cellulose fluff fibers and the second absorbent layer 13 to be made up of meltblown polypropylene. In another embodiment, the first absorbent layer 12 can be a composite comprised of meltblown fibers and a superabsorbent. The first absorbent layer 12 can also be a laminate comprised of a hydrocolloid material enclosed in a hydrophilic tissue, such as airlaid tissue. In another embodiment, at least one of the absorbent layers 12 or 13 may contain, along its periphery, a fluid-tight seal which can be constructed out of a material which is the same as the baffle 14.

Referring again to FIG. 1, the second absorbent layer 13 is depicted having a length, as measured along longitudinal axis X—X, which is less than the length of the first absorbent layer 12. However, it is understood that this feature is an optional embodiment, and the length of the second absorbent layer 13 can be equal to, or greater than, the length of first absorbent layer 12. The second absorbent layer 13 should preferably be wider, along its central transverse axis Y—Y, than the first absorbent layer 12. This will enable a wearer to determine, from viewing the top surface 16 of the absorbent article 10, whether fluid has spread outward to the longitudinal side edges 18 and 19 of the second absorbent layer 13. If liquid has migrated outward to the edges 18 and 19, the user will know that it is time to replace the product.

The first absorbent layer 12 can have an hourglass or dogbone shape with a narrow portion in the middle. In such an embodiment, the second absorbent layer 13 can have an oval shape. Preferably, the first absorbent layer 12 will be thicker at the narrow, middle portion to provide added absorbency in this critical area. Most preferably, the first absorbent layer 12 will be thicker throughout than the second absorbent layer 13. Alternatively, the absorbent article 10 can have a uniform thickness with a higher absorbency material located in the center portion than at the ends. Higher absorbency may be achieved by using fibers of greater absorbency or by adding superabsorbents to the first absorbent layer 12.

Figure 2:
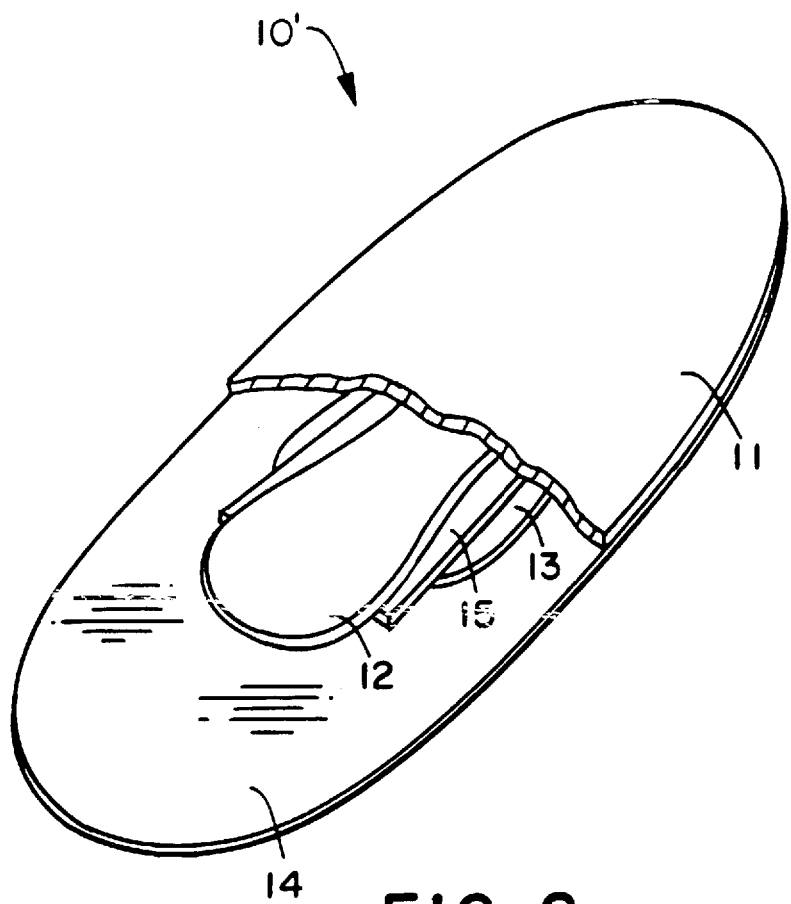
FIG. 2 is a perspective top view of another embodiment of an absorbent article having a portion cut away to show the inner construction thereof.

Referring to FIG. 2, an absorbent article 10' is depicted having a cover 11, a baffle 14, and first, second and third absorbent layers 12, 13 and 15, respectively. The third absorbent layer 15 is positioned between the first absorbent layer 12 and the second absorbent layer 13. The second absorbent layer 13 should have a higher transverse wicking rate than the third absorbent layer 15. The second absorbent layer 13 will preferably be wider, along its transverse central axis Y—Y, than the third absorbent layer 15. When the third absorbent layer 15 is positioned intermediate the absorbent layers 12 and 13, the third absorbent layer 15 will typically be the primary absorbent layer. As the primary absorbent layer, it will be thicker and have a higher absorbency rate than the first absorbent layer 12.

Figure 3:
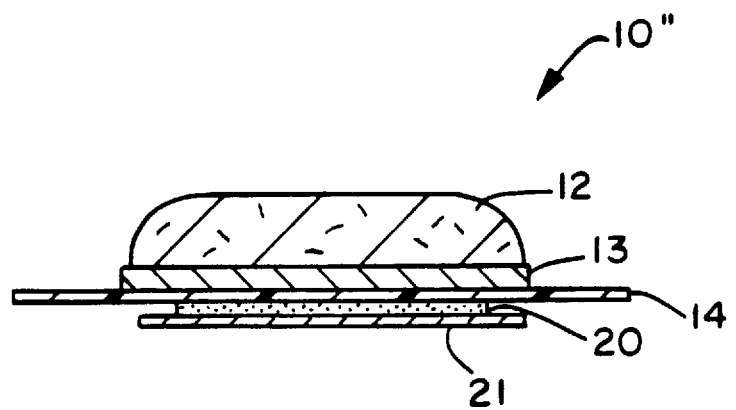
FIG. 3 is a cross-sectional view of another embodiment of an absorbent article taken across its transverse axis.

Referring to FIG. 3, an absorbent article 10" is shown which contains a first absorbent layer 12, a second absorbent layer 13 and a baffle 14. A longitudinally-extending garment adhesive strip 20 is attached to the exterior surface of the baffle 14 and is covered by a removable peel strip 21. The garment adhesive 20 is commercially available. One company that sells this adhesive is National Starch Co. located at 10 Finderne Ave. Bridgewater, N.J. 08807. The garment adhesive 20 is used to secure the absorbent article 10" to the inside of the crotch portion of an undergarment (not shown), so that it can be properly aligned to cover the vaginal opening. The peel strip 21 is releasably attached to the garment adhesive strip 20 to prevent the adhesive from becoming contaminated prior to attachment to the undergarment. The peel strip 21 can be a white Kraft paper, coated on one side so that it can be released from a hot melt adhesive. The peel strip 21 is designed to be removed by the ultimate consumer just prior to placement of the absorbent article 10" in the undergarment. It should be noted that, in FIG. 3, no cover is present. A cover is designed to be utilized in the preferred embodiment.

Figure 4:
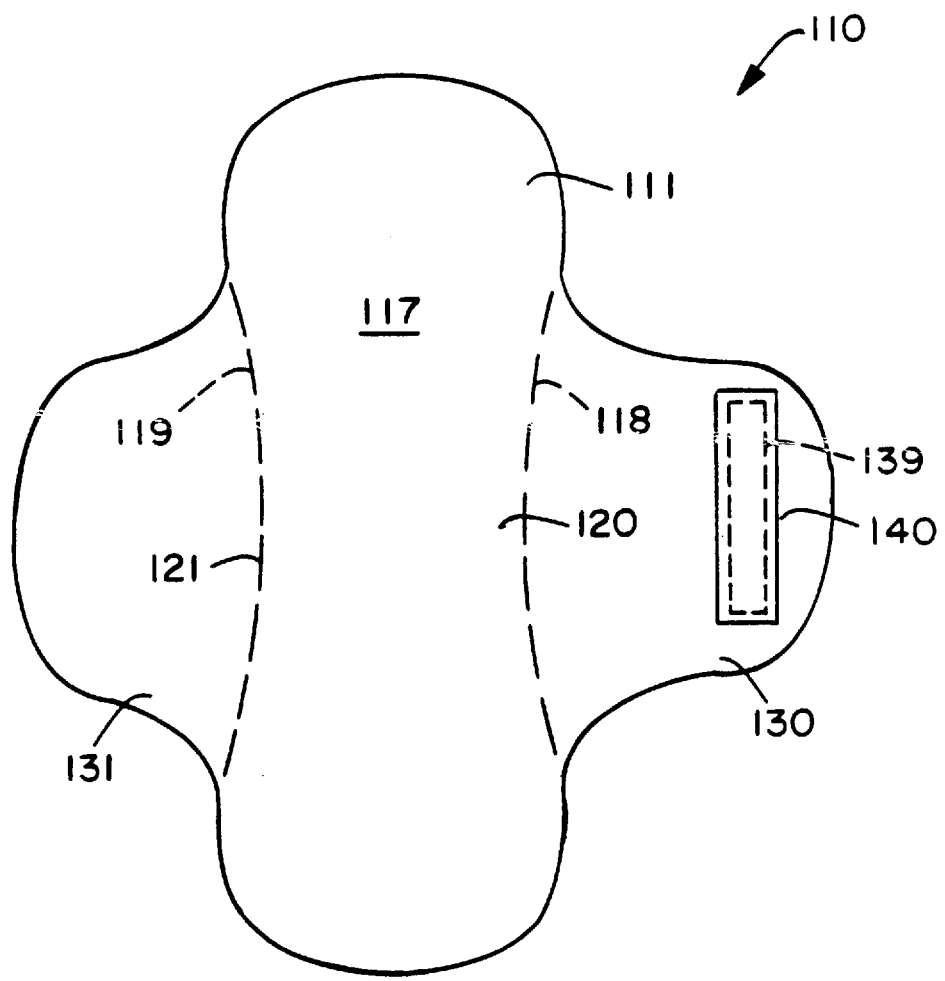
FIG. 4 is a perspective top view of another embodiment of an absorbent article having a portion cut away to show the inner construction thereof.

Referring to FIG. 4, an absorbent article 110 is shown which is similar in construction to the absorbent article 10 shown in FIG. 1. The absorbent article 110 has an hourglass-shaped, central absorbent 117 with two longitudinally extending side edges 118 and 119. Each of the side edges 118 and 119 has a concave central portion 120 and 121, respectively, shown by dotted lines. The absorbent article 110 further has two garment attachment panels 130 and 131, which extend outward from the central absorbent 117, along each of the concave central portions 120 and 121. The garment attachment panels 130 and 131 extend in a transverse direction outward from the central absorbent 117 and are designed to wrap around the outer surface of the crotch portion of an undergarment. The garment attachment panels 130 and 131 will extend laterally outward and lie in the same plane as the widest portion of the absorbent article 110. The garment attachment panels 130 and 131 can be constructed from the same materials as the baffle and/or the liquid-permeable cover 111.

Preferably, the garment attachment panels 130 and 131 will be an extension of both the baffle and the liquid-permeable cover 111. In an optional embodiment, at least one of the garment attachment panels 130 and 131 may have an adhesive strip 139, attached to its upper surface, which is covered by a releasable peel strip 140. The absorbent article 110 can also have at least one garment adhesive strip (not shown) secured to the central, exterior surface of the baffle, which can be covered by another releasable peel strip. When the consumer is ready to wear the product, the central peel strip is removed, and the absorbent article 110 is adhered to the inner surface of the undergarment via the garment adhesive. The consumer then removes the peel strip 140, attached to one of the garment attachment panels, and wraps the garment attachment panels 130 and 131 around the exterior surface of the undergarment. One garment attachment panel can then be adhered to the other garment attachment panel by the adhesive 139.

The garment attachment panels 130 and 131 preferably do not contain any absorbent material; although they could, if desired. The garment attachment panels 130 and 131 could be constructed of baffle material only. In such a case, it is desirable, for the comfort of the wearer, if a thin layer of absorbent material is placed on the body-facing side of at least one, and preferably both, garment attachment panels 130 and 131. In such a case, the baffle will preferably have an hourglass shape, with the garment attachment panels 130 and 131 extending from the narrow, central portion of the baffle and extending as far as the widest section of the absorbent article 110. When absorbent material is included in the garment attachment panels 130 and 131, it will not influence soiling, since the function of the walls formed by the garment attachment panels 130 and 131 is menstrual fluid containment rather than absorbency.

The absorbent layers contained in the absorbent article 110, rather than the garment attachment panels 130 and 131, will serve to absorb the vast majority of the menstrual fluid. Furthermore, with little or no absorbent material present in the garment attachment panels 130 and 131, the absorbent article 110 will be less bulky and more comfortable to the user.

Figure 5:
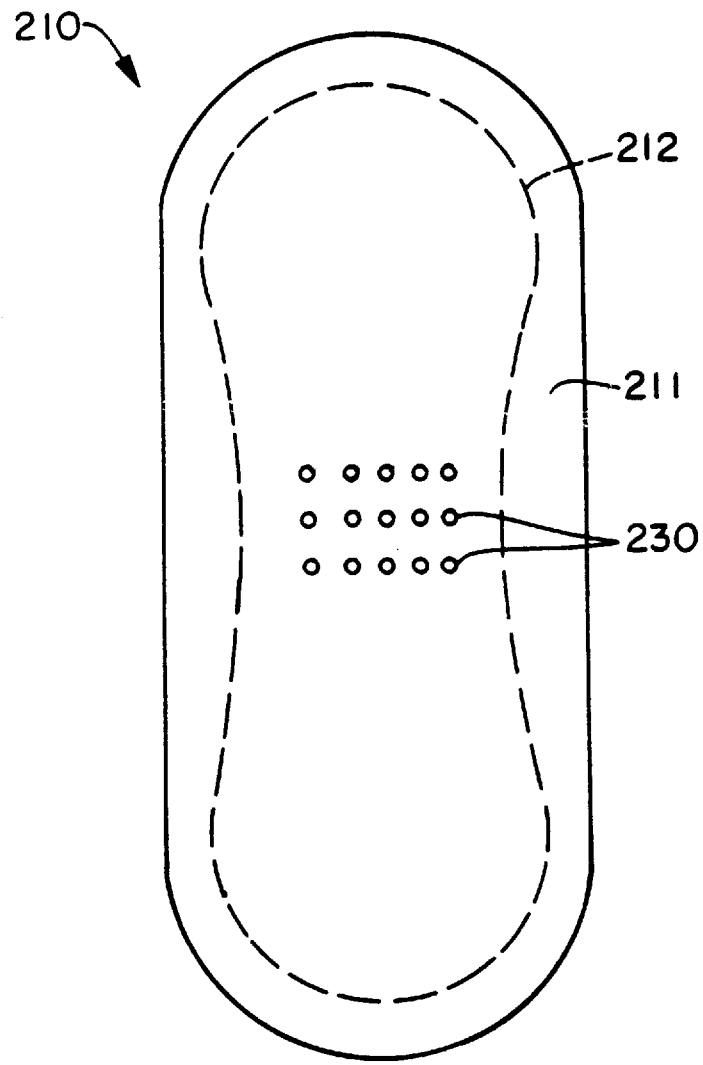
FIG. 5 is a perspective top view of another embodiment of an absorbent article having a portion cut away to show the inner construction thereof.

Referring to FIG. 5, an absorbent article 210 is illustrated which has a cover 211 and an hourglass-shaped first absorbent layer 212. The cover 211 contains a plurality of apertures or perforations 230 which are formed approximate the narrow portion of the absorbent article 210. The apertures 211 permit body fluid to rapidly pass down into the first absorbent layer 212.

Figure 6:
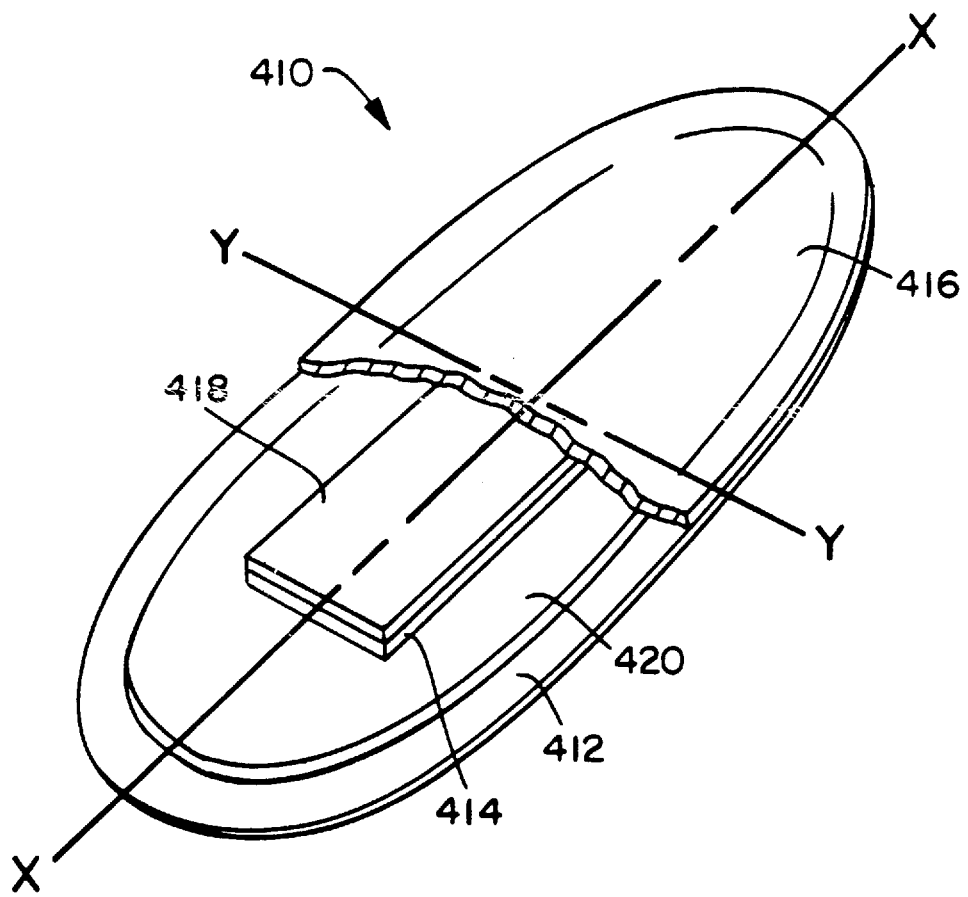
FIG. 6 is a partially cut away perspective view of another embodiment of an absorbent article showing the use of an intermediate baffle layer positioned between first and second absorbent layers.

Referring to FIG. 6, an absorbent article 410 is shown which includes a first liquid-impermeable baffle 412, a second liquid-impermeable baffle 414 and a liquid-permeable cover 416. The bottom surface of the first baffle 412 faces the user's undergarment, while the cover 416 faces the body of the user. A first absorbent layer 418 is positioned below the cover 416, and a second absorbent layer 420 is positioned on top of the first baffle 412. Preferably, the second baffle 414 is generally of the same shape as the first absorbent layer 418. The second absorbent layer 420 should have a higher transverse wicking rate than the first absorbent layer 418, and fluid staining on the second absorbent layer 420 will be visible through the cover 416. The first baffle 412 and the cover 416 can be coterminous and will define the exterior periphery of the absorbent article 410.

Construction adhesives, which adhere the various layers of the absorbent article to each other, and garment attachment adhesives, which adhere the absorbent article to the undergarment, may be any of those typically utilized in formation of sanitary napkins, diapers, training pants or incontinence garments. A preferred construction adhesive material is a hot-melt type adhesive, although other suitable adhesives may be used. A preferred method of attaching the absorbent article to an undergarment is by a single, wide band of adhesive which is selected for maximum attachment strength.

EXAMPLES

The following examples are being presented for the purpose of illustration only. In these examples, a modified U.S. government test #DDD-P-66B was followed. In our examples, the absorbency of an absorbent article was determined by laying the product on a flat, level, transparent surface, so that the underside of the absorbent article could be observed. A mirror was placed under the suspended surface to facilitate the observation of the underside of the absorbent article. A one percent (1%) dye solution of distilled water was applied to the center of the product. The temperature of the dye solution was 73° F., ±3°. The dye solution was applied from a burette at the rate of 15 milliliters/minute, ±3 ml, from a height of approximately one inch. A total insult of 5 ml of dye solution, for the Examples in Table 1, and 10 ml of dye solution, for the Examples in Table 2, was applied. The width and length of the stain in each Example was measured after 5 and 10 minutes, respectively, total elapsed time.

Referring to Table 1, the size of a liquid stain for a 5 milliliter (ml) insult of solution after 5 and 10 minutes, respectively, for different types of a single material is shown. The first entry is "Blotting Paper, unscored (75% Bleached Softwood, 25% Northern Pine)". The dimension of the first test sample was 60 millimeters (mm) wide by 182 mm long. The liquid stain, after five minutes, was 47 mm wide by 89 mm long and, after 10 minutes, was 47 mm wide by 93 mm long. Table 1 is for reference purposes only and is not illustrative of the present invention.

Referring to Table 2, which is illustrative of the present invention (except Example 12), stain dimensions for a 10 ml insult of solution on various materials is shown. Each material was placed under the fluff pulp core taken from a Kotex® Maxi Pad. The dimension of the fluff pulp core taken out of the Kotex® Maxi Pad was approximately 60 mm. wide by 150 mm. in length. The first entry (Example 10) was "Blotting Paper unscored (75% Bleached Softwood, 25% Northern Pine)." Two sets of data are shown. The first set of data (the first two horizontal rows) is for the second absorbent layer oriented in the "machine direction." By "machine direction," it is meant that the second absorbent layer was aligned parallel to the longitudinal axis of the absorbent article. "Cross direction" means that the second absorbent layer was aligned perpendicular to the longitudinal axis of the absorbent article. A sample 60 mm wide by 178 mm long was placed under the first absorbent layer. After 5 minutes, the stain on the first absorbent layer was 44 mm wide by 55 mm long, while the stain on the second absorbent layer was 60 mm wide by 123 mm long. After 10 minutes, the stain sizes were 46 mm wide by 59 mm long, and 60 mm wide by 133 mm long, respectively. Accordingly, this sample is an example of the present invention.

The second set of data for Example 10, listed in Table 2, (the third and fourth horizontal rows) is for the second absorbent layer oriented in a cross direction. This data demonstrates even more transverse wicking in the second absorbent layer. After 5 minutes, the stain sizes were 125 mm wide by 60 mm long; and after 10 minutes, the stain sizes were 150 mm wide by 60 mm long. Example 10 (60 grams per square meter (gsm) of meltblown polypropylene with surfactant treatment) demonstrates the greatest wicking properties and represents one preferred embodiment of this invention.

It should be noted that the cross direction orientation of the material in the second absorbent layer enhances the lateral fluid-distribution properties of that layer, see examples 10 and 11. It should also be mentioned that, for Example 12, the second absorbent layer did not wick fluid as far as the first absorbent layer and, therefore, is not an example of this invention.

TABLE 1

| Example | Material | Dimension of Mat'l. In mm | Stain After 5 Min. (mm) | Stain After 10 Min. (mm) |
|---|---|---|---|---|
| 1 | BLOTTING PAPER UNSCORED (75% BLEACHED SOFTWOOD, 25% NORTHERN PINE) | W = 60 L = 182 | W = 47 L = 89 | W = 47 L = 93 |
| 2 | BLOTTING PAPER SCORED (75% BLEACHED SOFTWOOD, 25% NORTHERN PINE) | W = 63 L = 125 | W = 45 L = 88 | W = 47 L = 91 |
| 3 | GELOK 8007 A/A SAB-840 | W = 63 L = 169 | W = 44 L = 45 | W = 45 L = 45 |
| 4 | BG 13 gsm 2 PLY TISSUE (100% LONGLAC SOFTWOOD) | W = 150 L = 180 | W = 139 L = 93 | W = 142 L = 99 |
| 5 | BG 13 gsm 4 PLY TISSUE (100% LONGLAC SOFTWOOD) | W = 150 L = 233 | W = 111 L = 67 | W = 117 L = 74 |
| 6 | KLEENEX ® TISSUE (30% SOFTWOOD 70% HARDWOOD) | W = 219 L = 228 | W = 151 L = 107 | W = 156 L = 108 |
| 7 | HI DRI ® PAPER TOWEL (100% RE-PROCESSED PULP) | W = 113 L = 282 | W = 100 L = 172 | W = 103 L = 178 |
| 8 | 60 gsm MELTBLOWN (POLYPROPYLENE) INSERT FROM NEW FREEDOM ® MAXI | W = 154 L = 152 | W = 52 L = 64 | W = 53 L = 66 |
| 9 | KOTEX ® MAXI FLUFF INSERT | W = 58 L = 152 | W = 35 L = 44 | W = 38 L = 48 |

TABLE 2

| Example | Composition of Second Absorbent Layer | Dimensions of Second Abs. Layer In mm | Stain on First Abs. Layer In mm 5 Min | Stain on First Abs. Layer In mm 10 Min | Stain on Second Abs. Layer In mm 5 Min | Stain on Second Abs. Layer In mm 10 Min |
|---|---|---|---|---|---|---|
| 10 | BLOTTING PAPER UNSCORED (75% BLEACHED SOFTWOOD, 25% NORTHERN PINE) | W = 60 L = 178 W = 357 L = 60 | W = 44 L = 55 W = 28 L = 36 | W = 46 L = 59 W = 35 L = 42 | W = 60 L = 123 W = 125 L = 60 | W = 60 L = 133 W = 150 L = 60 |
| 11 | BLOTTING PAPER SCORED (75% BLEACHED SOFTWOOD, 25% NORTHERN PINE) | W = 64 L = 250 W = 175 L = 65 | W = 34 L = 55 W = 31 L = 38 | W = 35 L = 60 W = 35 L = 42 | W = 51 L = 110 W = 145 L = 60 | W = 53 L = 118 W = 162 L = 66 |
| 12 | GELOK 8007 A/A SAB-840 | W = 64 L = 190 | W = 40 L = 55 | W = 44 L = 64 | W = 31 L = 33 | W = 34 L = 33 |
| 13 | BG 13 gsm 2 PLY TISSUE (100% LONGLAC SOFTWOOD) | W = 151 L = 166 | W = 44 L = 44 | W = 49 L = 45 | W = 97 L = 80 | W = 100 L = 87 |
| 14 | BG 13 gsm 4 PLY TISSUE (100% LONGLAC SOFTWOOD) | W = 151 L = 166 | W = 33 L = 42 | W = 39 L = 44 | W = 104 L = 83 | W = 113 L = 94 |
| 15 | KLEENEX ® TISSUE (30% SOFTWOOD 70% HARDWOOD) | W = 219 L = 228 | W = 42 L = 45 | W = 44 L = 46 | W = 131 L = 126 | W = 150 L = 143 |
| 16 | HI DRI ® PAPER TOWEL (100% RE-PROCESSED PULP) | W = 113 L = 282 | W = 44 L = 42 | W = 48 L = 44 | W = 80 L = 109 | W = 88 L = 112 |

TABLE 2-continued

| Example | Composition of Second Absorbent Layer | Dimensions of Second Abs. Layer In mm | Stain on First Abs. Layer In mm 5 Min | Stain on First Abs. Layer In mm 10 Min | Stain on Second Abs. Layer In mm 5 Min | Stain on Second Abs. Layer In mm 10 Min |
|---|---|---|---|---|---|---|
| 17 | 60 gsm MELTBLOWN (POLYPROPYLENE) INSERT FROM NEW FREEDOM ® MAXI | W = 154 L = 152 | W = 37 L = 41 | W = 40 L = 42 | W = 165 L = 136 | W = 126 L = 143 |

The ratios of the width of the stain, for the materials listed in Table 2, were calculated over a predetermined time period. Accordingly, the "transverse wicking rate" is equal to the stain width per unit time. The ratios are listed in Table 3 below for time periods of 5 and 10 minutes, respectively. The ratio is obtained by dividing the value for the second absorbent layer by the value of the first absorbent layer. For example, for Example 10 in the cross direction at 5 minutes, 125/28=4.5 rounded to one place after the decimal point.

TABLE 3

| Example | Stain width in 1st Layer (mm) 5 Min | Stain width in 1st Layer (mm) 10 Min | Stain width in 2nd Layer (mm) 5 Min | Stain width in 2nd Layer (mm) 10 Min | Ratio 5 Min. | Ratio 10 Min. | Comments |
|---|---|---|---|---|---|---|---|
| 10 MD | 44 | 46 | 60 | 60 | X | X | Note 1 |
| CD | 28 | 35 | 125 | 150 | 4.5 | 4.3 | |
| 11 MD | 34 | 35 | 51 | 53 | 1.5 | 1.5 | |
| CD | 31 | 53 | 145 | 162 | 4.7 | 3.1 | |
| 12 MD | 40 | 44 | 31 | 34 | X | X | Note 2 |
| 13 MD | 44 | 49 | 97 | 100 | 2.2 | 2.8 | |
| 14 MD | 33 | 39 | 104 | 113 | 3.2 | 2.9 | |
| 15 MD | 42 | 44 | 131 | 150 | 3.1 | 3.4 | |
| 16 MD | 44 | 48 | 80 | 88 | 1.8 | 1.8 | |
| 17 MD | 37 | 40 | 165 | 126 | 4.5 | 3.2 | |

MD = machine direction
CD = cross direction
Note 1: X indicates that a ratio was not calculated because the stain reached the longitudinal edges of the second absorbent layer.
Note 2: X indicates that a ratio was not calculated because the stain was smaller on the second layer than on first layer.

One will notice that the ratio of the transverse wicking rate of the second absorbent layer, when aligned in a machine direction, to the first absorbent layer is greater than about 1.5 after 5 minutes, and greater than about 1.5 after 10 minutes. One will also notice that the ratio of the transverse wicking rate of the second absorbent layer, when aligned in a cross direction, to the first absorbent layer is greater than about 4.5 after 5 minutes and greater than about 3.1 after 10 minutes.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A sanitary napkin having a central transverse axis and a generally hourglass configuration with longitudinal edges each having a concave central portion comprising:
   a) a liquid-permeable cover;
   b) a liquid-impermeable baffle;
   c) a first absorbent layer positioned between said cover and said baffle;
   d) a second absorbent layer positioned between said first absorbent layer and said baffle; said first and second absorbent layers being enclosed by said cover and said baffle, said second absorbent layer having a higher transverse wicking rate than said first absorbent layer;
   e) a third absorbent layer positioned between said first and second absorbent layers, said third absorbent layer having a width measured along said central transverse axis which is greater than said first absorbent layer but less than said second absorbent layer and said third absorbent layer having a transverse wicking rate which is less than a transverse wicking rate of said second absorbent layer; and
   f) a pair of garment attachment panels integrally formed from said cover and said baffle, said garment attachment panels extending laterally from said concave central portion of each of said longitudinal edges and laying in the same plane as the widest portion of said sanitary napkin.

2. An absorbent article for absorbing body fluid having a central transverse axis, said absorbent article comprising:
   a) a first absorbent layer;
   b) a second absorbent layer having an oval configuration with a higher transverse wicking rate than said first absorbent layer, said second absorbent layer having a width measured along said central transverse axis which is greater than that of said first absorbent layer; and
   c) a third absorbent layer positioned between said first and second absorbent layers, said third absorbent layer having a width measured along said central transverse axis which is greater than said first absorbent layer but less than said second absorbent layer and a transverse wicking rate which is less than said second absorbent layer, said greater width and higher transverse wicking rate of said second absorbent layer enabling body fluid to be transversely routed in said second absorbent layer faster than in either said first or third absorbent layers whereby a user can visually inspect said absorbent article to determine if said absorbent article is approaching its maximum fluid capacity.

3. The absorbent article of claim 2 wherein said first absorbent layer contains a superabsorbent and said second absorbent layer has a thickness less than that of said first absorbent layer.

4. The absorbent article of claim 2 wherein said second absorbent layer contains a superabsorbent.

5. The absorbent article of claim 2 wherein the transverse wicking rate ratio of said second absorbent layer to said first absorbent layer is greater than about 1.5 after 5 minutes.

6. The absorbent article of claim 2 wherein the transverse wicking rate ratio of said second absorbent layer, when aligned in a cross direction, to said first absorbent layer is greater than about 3.1 after 10 minutes.

7. The absorbent article of claim 2 wherein the transverse wicking rate ratio of said second absorbent layer, when aligned in a machine direction, to said first absorbent layer is greater than about 1.5 after 10 minutes.

8. An absorbent article for absorbing body fluid having a central transverse axis, said absorbent article comprising:
   a) a first absorbent layer;
   b) a second absorbent layer having a width measured along said central transverse axis which is greater than that of said first absorbent layer, said second absorbent layer having a higher transverse wicking rate than said first absorbent layer; and
   c) a third absorbent layer positioned between said first and second absorbent layers, said third absorbent layer having a width measured along said central transverse axis which is greater than said first absorbent layer but less than said second absorbent layer and a transverse wicking rate which is less than said second absorbent layer, said greater width and higher transverse wicking rate of said second absorbent layer enabling body fluid to be transversely routed in said second absorbent layer faster than in either said first or third absorbent layers whereby a user can visually inspect said absorbent article to determine if said absorbent article is approaching its maximum fluid capacity.

9. The absorbent article of claim 8 wherein said third absorbent layer has a thickness greater than said first and second absorbent layers.

10. The absorbent article of claim 8 wherein said first absorbent layer has an hourglass configuration, said second absorbent layer has an oval configuration and said third absorbent layer has a rectangular configuration.

11. The absorbent article of claim 8 wherein said second and third absorbent layers contain a superabsorbent.

12. An absorbent article for absorbing body fluid having a central transverse axis and a generally hourglass configuration with a pair of longitudinal edges each having a concave central portion, said absorbent article comprising:
   a) a first absorbent layer;
   b) a second absorbent layer having an oval configuration with a thickness less than that of said first absorbent layer and a width measured along said central transverse axis which is greater than that of said first absorbent layer, said second absorbent layer having a higher transverse wicking rate than said first absorbent layer;
   c) a third absorbent layer positioned between said first and second absorbent layers, said third absorbent layer having a width measured along said central transverse axis which is greater than said first absorbent layer but less than said second absorbent layer, said greater width and higher transverse wicking rate of said second absorbent layer enabling body fluid to be transversely routed in said second absorbent layer faster than in either said first or third absorbent layers whereby a user can visually inspect said absorbent article to determine if said absorbent article is approaching its maximum fluid capacity; and
   d) a pair of garment attachment panels extending laterally outwardly from one of said concave central portions and lying in the same plane as the widest portion of said absorbent article.

* * * * *